US012710392B2

(12) United States Patent
Lesso

(10) Patent No.: US 12,710,392 B2
(45) Date of Patent: Aug. 18, 2026

(54) CIRCUITRY FOR ELECTROCHEMICAL CELLS

(71) Applicant: Cirrus Logic International Semiconductor Ltd., Edinburgh (GB)

(72) Inventor: John P. Lesso, Edinburgh (GB)

(73) Assignee: Cirrus Logic Inc., Austin, TX (US)

(*) Notice: Subject to any disclaimer, the term of this patent is extended or adjusted under 35 U.S.C. 154(b) by 804 days.

(21) Appl. No.: 17/725,995

(22) Filed: Apr. 21, 2022

(65) Prior Publication Data

US 2023/0341348 A1 Oct. 26, 2023

(51) Int. Cl.

| | |
|---|---|
| ***A61B 5/145*** | (2006.01) |
| ***A61B 5/00*** | (2006.01) |
| ***A61B 5/1468*** | (2006.01) |
| ***A61B 5/1486*** | (2006.01) |
| ***G01N 27/327*** | (2006.01) |
| ***H03M 1/12*** | (2006.01) |

(52) U.S. Cl.

CPC ....... *G01N 27/3273* (2013.01); *A61B 5/0002* (2013.01); *A61B 5/14532* (2013.01); *A61B 5/14542* (2013.01); *A61B 5/14546* (2013.01); *A61B 5/1468* (2013.01); *A61B 5/1486* (2013.01); *A61B 5/7225* (2013.01); *H03M 1/125* (2013.01); *A61B 2560/0209* (2013.01)

(58) Field of Classification Search

CPC ............ G01N 27/3273; A61B 5/14532; A61B 5/14542; A61B 5/14546; A61B 5/1468; A61B 5/1486; A61B 5/7225

See application file for complete search history.

(56) References Cited

U.S. PATENT DOCUMENTS

| | | | | |
|---|---|---|---|---|
| 8,552,771 | B1 | 10/2013 | Jordan et al. | |
| 11,251,807 | B1 * | 2/2022 | Ren | H03M 3/458 |
| 2008/0255808 | A1 * | 10/2008 | Hayter | A61B 5/6843 708/300 |
| 2014/0020445 | A1 * | 1/2014 | Waters | G01C 23/00 73/1.01 |

FOREIGN PATENT DOCUMENTS

| | | | |
|---|---|---|---|
| EP | 0824291 | B1 | 2/1998 |
| JP | 2015103820 | A | 6/2015 |
| WO | 2020186265 | A1 | 9/2020 |

OTHER PUBLICATIONS

J. Van Assche and G. Gielen, "Power Efficiency Comparison of Event-Driven and Fixed-Rate Signal Conversion and Compression for Biomedical Applications," in IEEE Transactions on Biomedical Circuits and Systems, vol. 14, No. 4, pp. 746-756, Aug. 2020 (Year: 2020).*

Combined Search and Examination Report under Sections 17 and 18(3), UKIPO, Application No. GB2305097.4, mailed Sep. 19, 2023.

Examination Report under Sections18(3), UKIPO, Application No. GB2305097.4, mailed Apr. 4, 2024.

* cited by examiner

*Primary Examiner* — Jason M Sims
*Assistant Examiner* — Kyle W. Kretzer
(74) *Attorney, Agent, or Firm* — Jackson Walker L.L.P.

(57) ABSTRACT

Circuitry for processing an analyte signal obtained from an electrochemical cell, the circuitry comprising: a first analog-to-digital converter (ADC) configured to generate a first digital output based on the analyte signal; a second ADC configured to generate a second digital output based on the analyte signal; and control circuitry configured to control generation of the second digital output by the second ADC based on the first digital output from the first ADC.

28 Claims, 5 Drawing Sheets

CIRCUITRY FOR ELECTROCHEMICAL CELLS

TECHNICAL FIELD

The present disclosure relates to circuitry for electrochemical cells.

BACKGROUND

Electrochemical sensors are widely used for the detection of one or more particular chemical species, analytes, indirectly via the detection of an oxidation or reduction current. Such sensors comprise an electrochemical cell, consisting of two or more electrodes configured for contact with an analyte whose concentration is to be ascertained. Such sensors also comprise circuitry for driving one or more of the electrodes and for measuring a response at one or more of the electrodes.

Conventional measurement circuitry in electrochemical sensors comprises several amplifiers, feedback and/or feedback loops in addition to an analog-to-digital converters (ADCs) configured to periodically sample one or more voltage at the electrochemical sensor. Periodic sampling using high resolution ADCs is relatively intensive and can therefore utilise large amounts of power. When electrochemical sensors are battery powered, for example when used in continuous glucose monitoring, it is desirable for such sensors to use as little power as possible.

SUMMARY

According to a first aspect of the disclosure, there is provided circuitry for processing an analyte signal obtained from an electrochemical cell, the circuitry comprising: a first analog-to-digital converter (ADC) configured to generate a first digital output based on the analyte signal; a second ADC configured to generate a second digital output based on the analyte signal; and control circuitry configured to control generation of the second digital output by the second ADC based on the first digital output from the first ADC.

The second ADC may have a higher resolution than the first ADC.

The first ADC may consume less power when generating the first digital output than the second ADC consumes when generating the second digital output.

The first ADC may be an event driven ADC.

The first ADC may be asynchronous.

The first ADC may comprise a comparator configured to compare the analyte signal with a first reference voltage.

The first ADC may be configured to sample the analyte signal at a first sampling rate and the second ADC may be configured to sample the analyte signal at a second sampling rate slower than the first sampling rate.

The control circuitry may be configured to control generation of the second digital output by the second ADC in response to a change in the first digital output from the first ADC.

The control circuitry may be configured to control generation of the second digital output by the second ADC in response to the change in the first digital output from the first ADC exceeding a threshold change.

The control circuitry may be configured to control generation of the second digital output by the second ADC in response to a rate of change in the first digital output from the first ADC exceeding a threshold rate.

The control circuitry may be configured to control generation of the second digital output by the second ADC in response to the first digital output falling below a threshold limit.

The control circuitry may be configured to increase a sampling rate of the second ADC in response to an increase in the first digital output.

The control circuitry may be configured to control generation of the second digital output by the second ADC in response to the change in the first digital output from the first ADC being below a change threshold during a change interval. For example, the control circuitry may be configured to decrease a sampling rate of the second ADC in response to the change being below the change threshold over the change interval.

Controlling generation of the second digital output by the second ADC may comprise: triggering the second ADC to sample the analyte signal to generate the second digital output.

Controlling generation of the second digital output by the second ADC may comprise: powering up or activating the second ADC.

The circuitry may further comprise: a transmitter configured to transmit one or more of an interrupt signal, the first digital output and the second digital output to a host device. The control circuitry may be configured to control the transmitter to transmit an interrupt signal to a host device based on the first digital output from the first ADC.

The control circuitry may be configured to control the transmitter to transmit an interrupt signal to a host device based on a value of a second digital output from the second ADC. The control circuitry may be configured to control the transmitter to transmit the interrupt signal to the host device if the second digital output is within a threshold range of the first digital output.

The control circuitry may be configured to combine the first digital output with the second digital output between updates of second digital output by the second ADC.

According to another aspect of the disclosure, there is provided circuitry for processing an analyte signal obtained from an electrochemical cell, the circuitry comprising: a first analog-to-digital converter (ADC) configured to generate a first digital output based on the analyte signal; a second ADC configured to periodically generate a second digital output based on; and a control module configured to: monitor the first digital output between periodic generation of the analyte signal by the second ADC; and in response to the first digital output meeting one or more criteria, output an interrupt signal.

The one or more criteria may comprise one or more of: a) the first digital output falling below a threshold level; b) the first digital output exceeding a threshold level; c) the first digital output moving outside of a threshold range; d) the first digital output changing at a rate exceeding a threshold rate.

The first ADC may be configured to periodically generate the first digital output at a first sampling rate. The second ADC may be configured to periodically generate the second digital output at a second sampling rate slower than the first sampling rate.

The first ADC may be asynchronous, or event driven.

The interrupt signal may be output to the second ADC.

The circuitry may further comprise a transmitter. The interrupt signal may be output to the transmitter.

The analyte may be one of glucose, a ketone, oxygen or a lactate.

According to another aspect of the disclosure, there is provided an analyte sensor comprising circuitry as described above.

The analyte sensor may be an electrochemical aptamer-based sensor.

Alternatively, the analyte sensor may be a glucose oxidase-based sensor.

According to another aspect of the disclosure, there is provided a system comprising the analyte sensor described above; and a host device in wireless communication with the analyte sensor.

The host device may comprise one of a mobile computing device, a laptop computer, a tablet computer, a games console, a remote control device, a home automation controller or a domestic appliance, a toy, a robot, an audio player, a video player, or a mobile telephone, and a smartphone.

According to another aspect of the disclosure, there is provided a continuous glucose monitor comprising the analyte sensor and/or circuitry as described above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Figure 1:
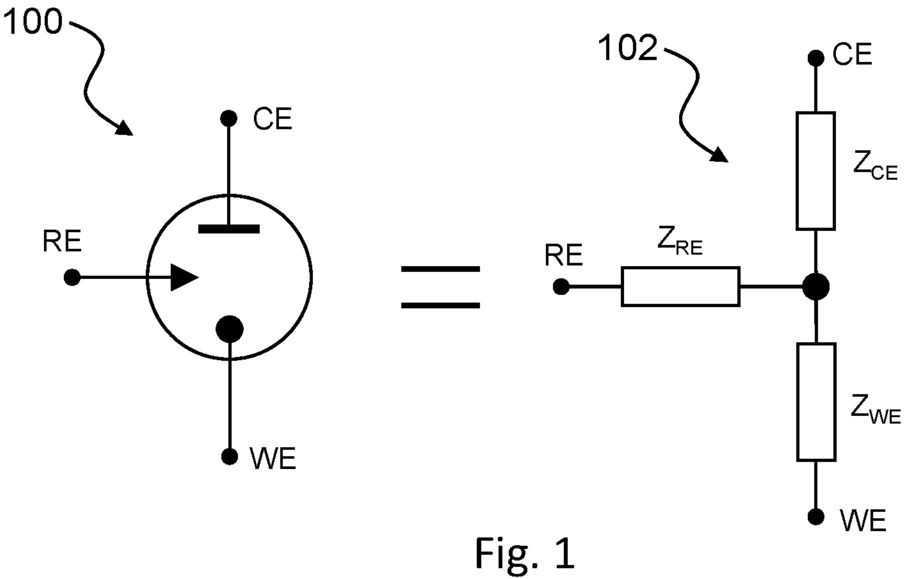
FIG. 1 illustrates a schematic diagram and electrical equivalent circuit for a three-electrode electrochemical cell.

FIG. 1 is a schematic diagram of an electrochemical cell 100 (also known as a potentiostats) comprising three electrodes, namely a counter electrode CE, a working electrode WE and a reference electrode RE. FIG. 1 also shows an equivalent circuit 102 for the electrochemical cell comprising a counter electrode inductance ZCE, a working electrode inductance ZWE and a reference electrode inductance ZRE.

To determine a characteristic of the electrochemical cell, and therefore an analyte concentration, a bias voltage is applied at the counter electrode CE and the resultant current at the working electrode is measured. The reference electrode RE is used to measure a voltage drop between the working electrode WE and the reference electrode RE. The bias voltage is then adjusted to regulate the voltage at the reference electrode. As the resistance in the cell 100 increases, the voltage drop measured at the reference electrode increases. In response, the measurement current injected at the counter electrode CE is decreased. Likewise, as the resistance in the cell 100 decreases, the voltage drop measured at the reference electrode decreases. In response, the measurement current injected at the counter electrode CE is increased. Thus the electrochemical cell 100 reaches a state of equilibrium where the voltage drop between the reference electrode RE and the working electrode WE is maintained constant. Since the current injected at the counter electrode CE and the voltage drop are known, the resistance of the cell 100 can be ascertained.

Figure 2:
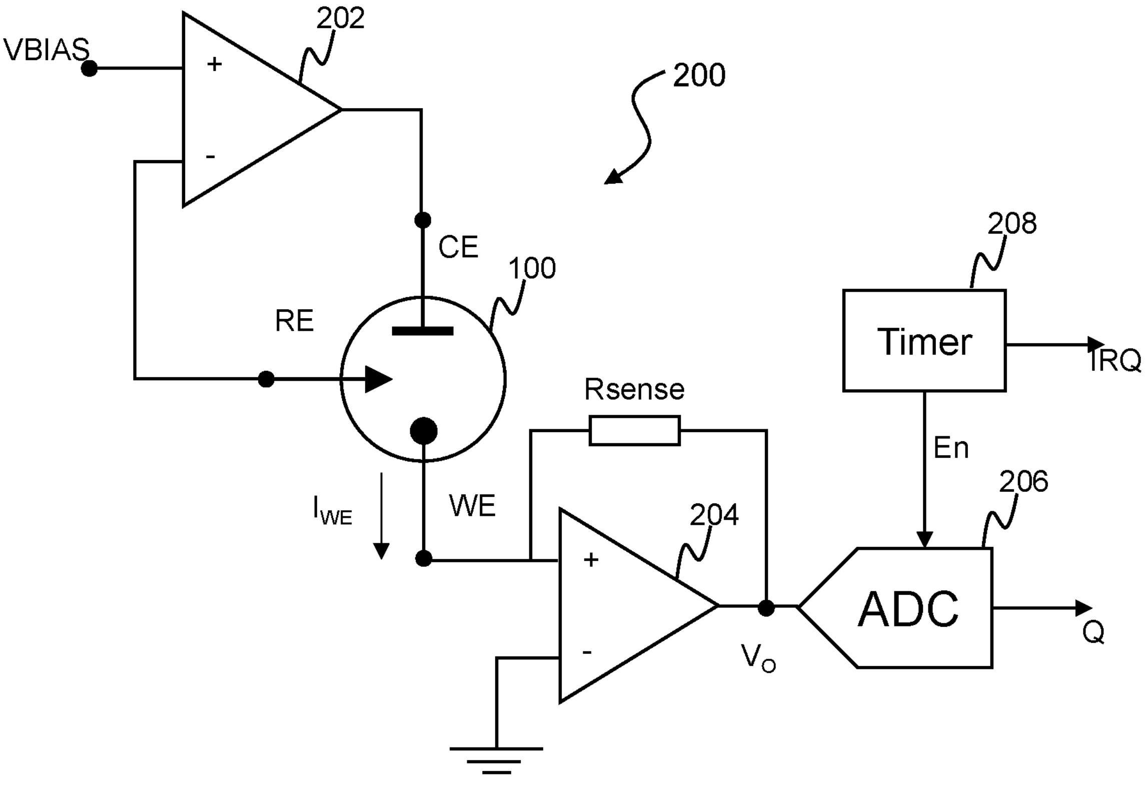
FIG. 2 is a schematic diagram of an example prior art measurement circuit.

FIG. 2 illustrates an example prior art drive and measurement circuit 200 which is configured to implement the above explained cell characterisation, specifically for measuring an analyte concentration in the electrochemical cell 100 shown in FIG. 1. The circuit 200 comprises a buffer 202 and an op-amp 204 configured as a transimpedance amplifier. A non-inverting input of the buffer 202 is coupled to a bias voltage VBIAS. An inverting input of the buffer 202 is coupled to the reference electrode RE. An output of the buffer 202 is coupled to the counter electrode CE and configured to inject the measurement current. The measurement current injected at the counter electrode CE by the buffer 202 is proportional to the difference between the bias voltage VBIAS and the voltage at the reference electrode RE. As such, the buffer 202 acts to maintain the voltage between the reference electrode RE and the working electrode WE close to the bias voltage VBIAS. A non-inverting input of the op-amp 204 is coupled to the working electrode WE and the inverting input of the op-amp 204 is coupled to a reference voltage, in this case ground. A feedback loop comprising a sense resistor RSENSE is coupled between the non-inverting input and an output of the op-amp 204. The op-amp 204 is thus operable to output a voltage VO which is proportional to the current IWE at the working electrode WE. The output voltage VO is then provided to an analog-to-digital converter (ADC) 206.

Figure 3:
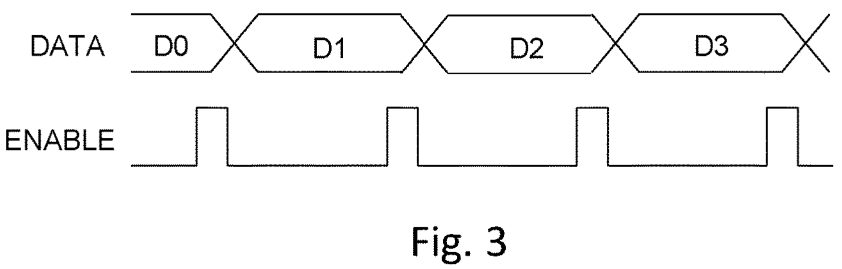
FIG. 3 is a signal diagram for the measurement circuit of FIG. 2.

The ADC 206 samples the output voltage VO and generates a digital output Q representing the current IWE at the working electrode WE. The ADC 206 samples the output voltage VO in response to receipt of an enable signal EN which is periodically output by a timer 208. Waveforms for the digital data signal DATA output from the ADC 206 as well as the enable EN provided to the ADC 206 from the timer 208 are shown in FIG. 3.

By taking measurements periodically as opposed to continuously, the power consumption of the measurement circuit 200 is reduced. However, if a significant change in the characteristics of the cell occurs during the period between samples of the output voltage VO, such changes are not seen until the next update of the digital output Q.

Several situations exist in which it would be advantageous to achieve low power operation through the use of periodic sampling, whilst maintaining the ability to detect significant changes between periodic samples. Such situations include but are not limited to medical sensing and radiation monitoring. Continuous glucose monitoring is one example of medical sensing in which it is important to detect and quickly act upon large changes in glucose levels in the blood over time. In radiation detectors, it is also advantageous to detect large changes in radiation levels which may be harmful to a person in the vicinity of such radiation.

Embodiments of the present disclosure aim to address or at least ameliorate one or more of the above issues with prior art sensors by providing a multi-ADC measurement solution. Specifically, a relatively high-resolution, high-power ADC is provided in combination with a relatively low-resolution, low-power ADC, both ADCs configured to sample a signal output from an electrochemical cell under test. The relatively low-resolution, low-power ADC is provided to detect changes taking place during intervals between periodic sampling undertaken by the relatively high-resolution, high-power ADC. In doing so, the low-power periodic sampling regime described above may be maintained, whilst providing the ability to monitor for changes in electrochemical characteristics of a cell between periodic high-resolution samples.

Figure 4:
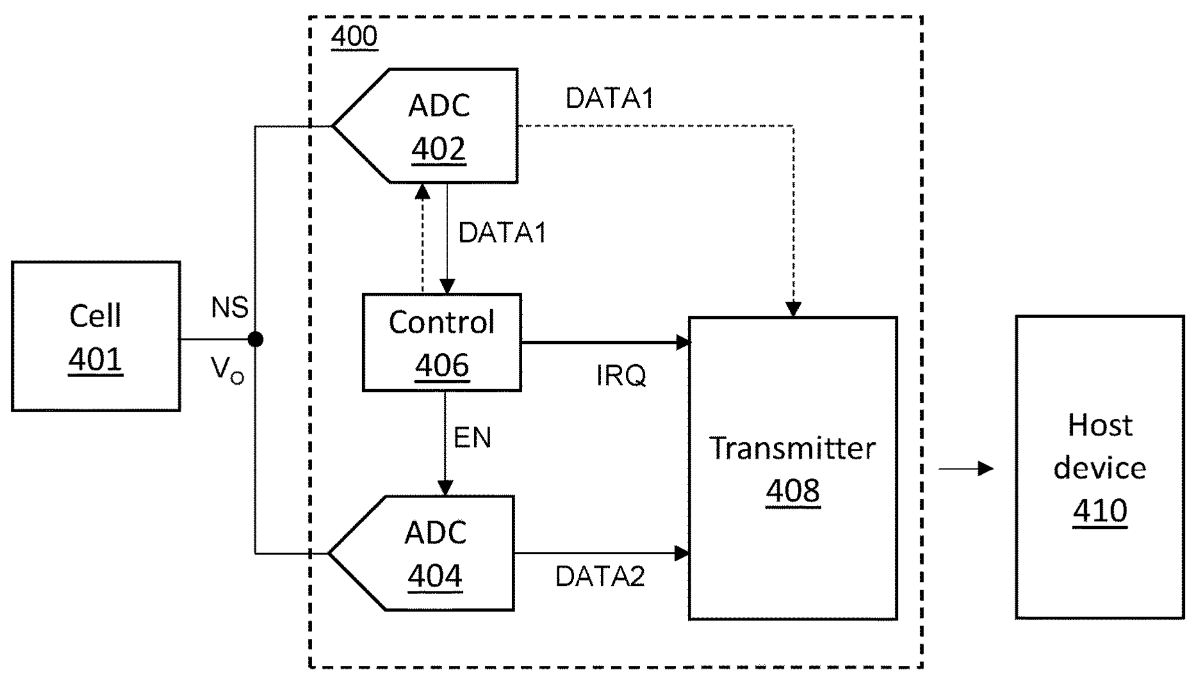
FIG. 4 is a schematic diagram of circuitry according to an embodiment of the present disclosure.

FIG. 4 schematically illustrates circuitry 400 for processing an analyte signal obtained from an electrochemical cell 401, such as the cell 100 shown in FIG. 2.

The circuitry 400 comprises a first ADC 402, a second ADC 404 and a control module 406. The first and second ADCs 402, 404 are each configured to sample voltage VO at a sampling node NS and generate respective first and second digital signals DATA1, DATA2 representing the sample voltage VO. The sample voltage VO is obtained, directly or indirectly, from the electrochemical cell 401. For example, the sample voltage VO may be generated from the non-inverting amplifier 204 shown in FIG. 2. Where the electrochemical cell 401 generates a current, that current may be sensed by an amplifier in a manner known in the art. In other embodiments, a voltage may be measured directly at the electrochemical cell 401.

The circuitry 400 may further comprise a transmitter 408 configured to receive an interrupt signal IRQ from the control module 406 and the second digital signal DATA2. Optionally, the first digital signal DATA1 from the first ADC 402 is provided to the transmitter 408. The transmitter 408 may be configured to transmit the second digital signal DATA2 (and optionally the first digital signal DATA1) to a host device 410. In some embodiments, the host device 410 may be a user device, such as a smartphone, a smartwatch, a tablet, a personal computer or the like. The interrupt signal IRQ provided from the control module 406 to the transmitter 408 may also be transmitted by the transmitter 408 to the host device 410. Alternatively, the interrupt signal IRQ may trigger the transmitter 408 to send the second digital signal DATA2 (and optionally the first digital signal DATA1) to the host device 410.

The circuitry 400 may be battery powered by a battery (not shown).

As mentioned above, the first ADC 402 and the second ADC 404 have different resolutions. Specifically, the first ADC 402 may have a lower resolution than the second ADC 404. The first ADC 402 may be faster than the second ADC 404 in generating a digital sample of the voltage VO at the sampling node NS. The first ADC 402 may consume less power than the second ADC 404. The first ADC 402 may therefore generate a cruder (i.e. less accurate) estimate of the voltage VO at the sampling node than the second ADC 402, but may consume less power in doing so.

The first ADC 402 may be configured to sample the sampling node NS periodically. Periodic sampling of the first ADC 402 may be controlled by the control module 406. Alternatively, the first ADC 402 may be configured to sample periodically without external control, such as control from the control module 406.

In some embodiments, the first ADC 402 is an event driven ADC (also known in the art as a level sensitive ADC or a level crossing ADC). Such an event driven ADC may be configured to output a sample result only on detection of a change in the voltage VO at the sampling node. Additionally or alternatively, such an event driven ADC may comprise a comparator to detect either a high or low signal level.

Figure 5:
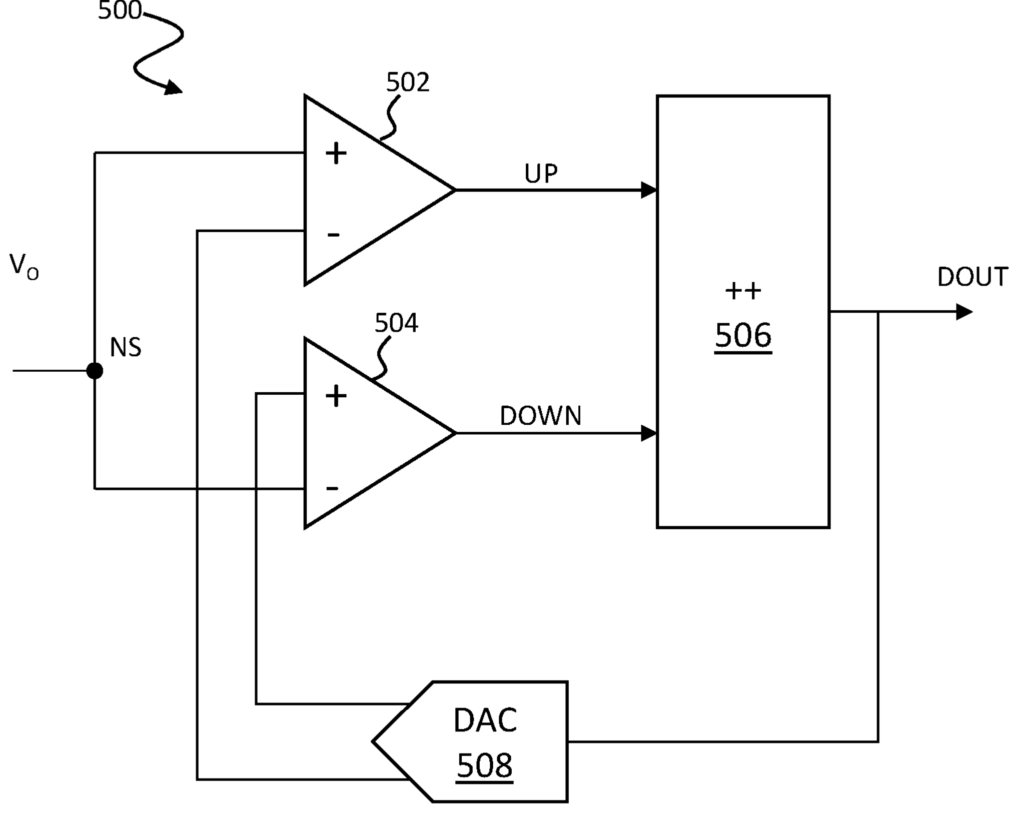
FIG. 5 is a schematic diagram of an example event driven ADC.

A known architecture for an event driven ADC 500 is shown in FIG. 5. The ADC 500 comprises a first comparator 502, a second comparator 504, a counter 506 and a digital-to-analog converter (DAC) 508. A non-inverting input of the first comparator 502 and an inverting input of the second comparator 504 are coupled to the sampling node. An inverting input of first comparator 502 and a non-inverting input of the second comparator 504 are coupled to the outputs of the DAC 508. Outputs of the first and second comparators 502, 504 are provided to the counter 506 which outputs a count value DOUT as the output of the ADC as well as being fed back to an input of the DAC 508. Each of the comparators 502, 504 compares the voltage VO at the sampling node NS with an analog representation of the count value DOUT output from the DAC 508. As the voltage VO at the sampling node NS increases, the output of the first comparator 502 is toggled high which in turn causes the counter 506 to increase its count value DOUT. This in turn increase the voltage provided from the DAC 508 and the output of the first comparator 502 returns low. As the voltage VO at the sample node NS decreases the output of the second comparator 504 is toggled low which in turn causes the counter 506 to decrease its count value DOUT. This in turn decreases the voltage provided from the DAC 508 and the output of the second comparator 504 return high. The counter 506 is preferably asynchronous so that no clock signal is required. In other embodiments, however, the counter 506 may be synchronous, clocked by an external clock (not shown).

Figure 6:
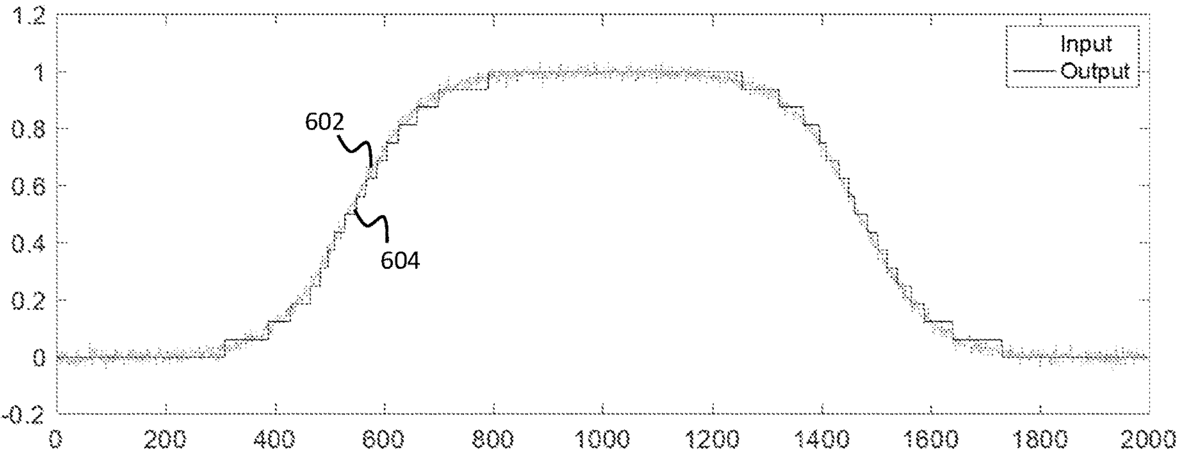
FIG. 6 is a schematic diagram of an example ADC.

FIG. 6 is a graph showing the voltage VO 602 at the sampling node NS and the output count value DOUT 604 at the output of the ADC 500.

Figure 7:
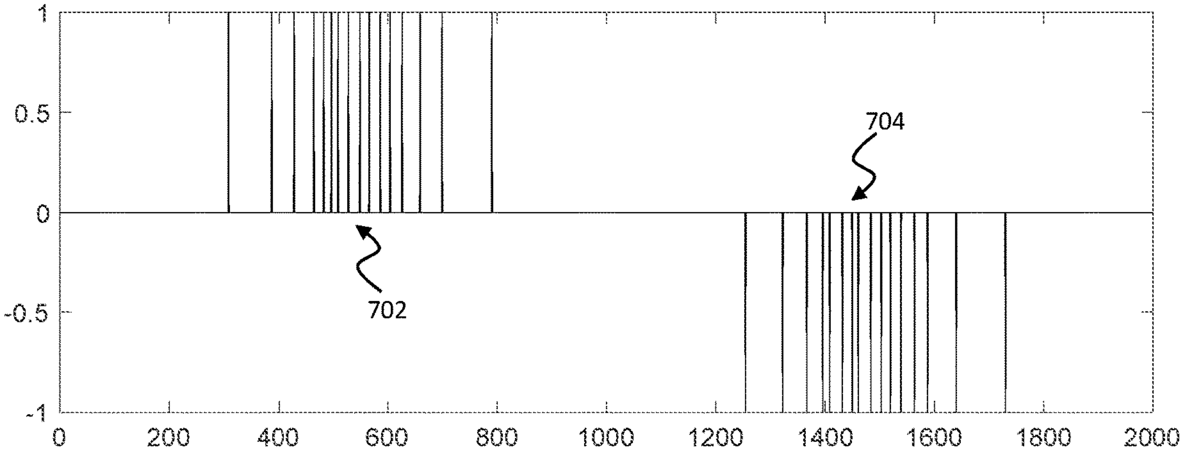
FIG. 7 is a graph of input voltage and output voltage of the ADC of FIG. 5 over time.
Figure 8:
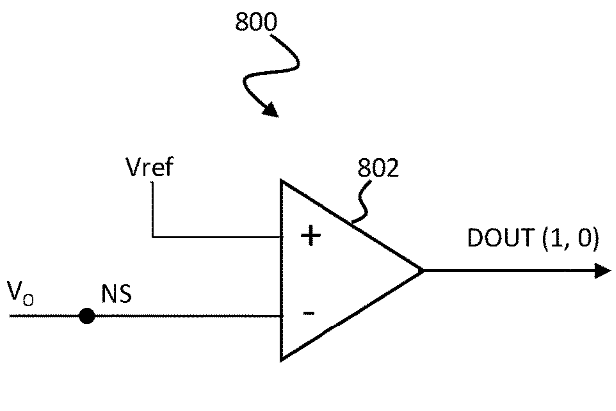
FIG. 8 is a graph of the output of the input of the counter of the ADC.

FIG. 7 illustrates the change in output 702, 704 at the first and second comparators 502, 504 in response to the voltage VO 602 shown in FIG. 6.

It can thus be seen that the output DOUT of the ADC 500 is driven by changes in the voltage VO at the sampling node NS. When the voltage VO is not changing, the ADC 500 is not active and thus is consuming very little power. Any power consumption is due to current leakage and may be in the order of nanowatts.

As mentioned above, in some embodiments, the ADC 402 may be implemented with a two-level output defining whether or not the voltage VO at the sampling node NS exceeds a threshold voltage. FIG. 6 is a schematic diagram of an example ADC 800 comprising a comparator 802 configured to compare the voltage VO at the sampling node NS with a reference voltage Vref. The sampling node NS is coupled to the inverting input of the comparator 802. The reference voltage Vref is provided to the non-inverting input of the comparator 802. When the output voltage VO at the sampling node NS falls below the reference voltage Vref, the output of the comparator 802 goes high (to 1 or Vdd). When the output voltage VO at the sampling node NS rises above the reference voltage Vref, the output of the comparator 802 goes low (to 0 of GND). When the electrochemical cell 401 is configured to measure glucose concentration, the reference voltage Vref may be set equal to an output voltage VO at the sampling node corresponding to hypoglycaemia (e.g. a glucose analyte concentration of around 4 mM/L). As such, the output of the ADC 800 may be configured to trigger high when glucose concentration falls below 4 mM/L, indicating the onset of hypoglycaemia.

In a variation of the ADC 800 shown in FIG. 6, the sampling node NS may be coupled to the non-inverting input of the comparator 802 and the reference voltage Vref coupled to the inverting input. In which case, the output levels will be switched, going high when the voltage VO at the sampling node NS rises above the reference voltage Vref and low when the voltage VO at the sampling node NS falls below the reference voltage.

In some embodiments, the first ADC 402 may comprise a pipelined ADC or a flash ADC or the like, such ADCs being very fast, but having relatively low resolution when compared to other ADC topologies. It will be appreciated, however, that such topologies tend to have higher power requirements than event driven topologies such as that described above with reference to FIG. 5. Such power requirements may be reduced by reducing mismatch requirements in such flash ADCs.

In some embodiments, the first digital output DATA1 of the first ADC 402 may be integrated into or added to the output of the second ADC 404. For example, the UP/DOWN outputs of the counter 506 of the ADC 500 or the high/low output DOUT of the ADC 600 may be integrated and/or added to the output of the second ADC 402. In doing so, the second digital output DATA2 may be updated without the need for the second ADC 404 to be enabled or activated.

In some embodiments, such functionality may be implemented by the control module 406 which may receive the first digital output DATA1 and integrate such data into the output of the second ADC 404. Alternatively, the above functionality may be implemented by an integration module 902 as shown in FIG. 9.

Figure 9:
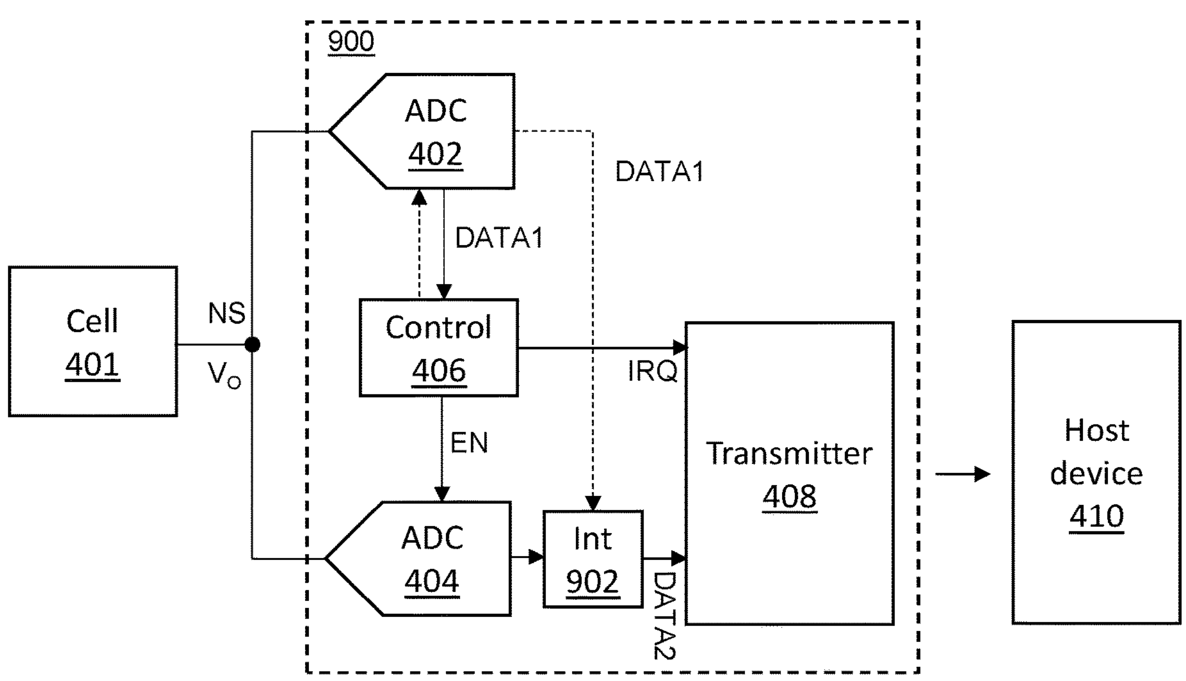
FIG. 9 is a schematic diagram of circuitry according to an embodiment of the present disclosure.

FIG. 9 schematically illustrates circuitry 900 which is a variation of the circuitry 400 shown in FIG. 4, like parts being given like numerals. The second ADC 404 may be activated or enabled periodically by the control module 406. Additionally, or alternatively, the second ADC 404 may be activated when the first digital output DATA1 from the first ADC 402 meets some criteria. Such criteria may include one or more of: the first digital output DATA1 exceeding a threshold; the first digital output DATA1 falling below a threshold; the first digital output DATA1 falling outside of a threshold range; the first digital output DATA1 changing at a rate exceeding a threshold rate. When this happens (i.e. on activation of the second ADC 404) the second ADC 404 may generate a fresh sample of the voltage VO. Thus, the integration module 902 may be configured to reset, outputting an unadulterated version of the second digital output DATA2 to the transmitter 408.

The addition or integration of the first digital output DATA1 into the second digital output DATA2 between sampling events of the second ADC 404 can allow tracking of the voltage VO at the sampling node in between measurements (preferably higher resolution measurements) by the second ADC 404.

Referring again to FIG. 4, as mentioned above, the second ADC 404 preferably has a higher resolution than the first ADC 402, so as to generate a more accurate sample of the voltage VO. The second ADC 404 may be relied upon for providing accurate readings of analyte concentration in the electrochemical cell 401. The second ADC 404 may incorporate any known high-resolution ADC topology. For example, the second ADC 404 may comprise a successive approximation (SAR) ADC or a delta-sigma ADC, such as an incremental delta-sigma ADC.

The control module 406 may be configured to output one or more interrupt signals IRQ based on one or more outputs of the first ADC 402. Additionally or alternatively, the control module 406 may be configured to control operation of the second ADC 404 based on one or more outputs from the first ADC 402.

In some embodiments, the control module 406 is configured to monitor a change in the first digital signal DATA1 output from the first ADC 402. For example, the control module 406 may monitor the first digital signal DATA1 and determine whether a change in the first digital signal DATA1 exceeds a predetermined change threshold. In another example, the control module 406 may output an interrupt signal ORQ or control operation of the second ADC 404 in response to any change in the first digital signal DATA1, no matter how large.

In some embodiments the control module 406 may be configured to output an interrupt signal IRQ if the first digital signal falls below a predetermined lower threshold. The threshold may be associated with a critical concentration of the analyte under test in the electrochemical cell 401. For example, where the analyte is glucose, if the concentration falls below a threshold, a hypoglycaemic event may be taking place. In this case, an interrupt may be output from the control module 406 if the glucose concentration in the electrochemical cell is indicative of the hypoglycaemic event.

In some embodiments the control module 406 may be configured to output an interrupt signal IRQ if the first digital signal rises above a predetermined upper threshold. The threshold may again be associated with a critical concentration of the analyte under test in the electrochemical cell 401. For example, where the analyte is a radioactive isotope, an increase in concentration of the isotope above the upper threshold may be indicative of a high level of radiation in the vicinity of the electrochemical cell 401. In this case, an interrupt may be output from the control module 406. Such interrupts may be output between periodic sampling performed by the second ADC 404.

In some embodiments, the control module 406 may be woken up by a change in the first digital signal DATA1 output from the ADC 402. For example, a change in the first digital signal DATA1 may cause the control module 406 to transition out of a low power state into a higher power state.

In some embodiments, the control module 406 may be configured to adapt operation of the second ADC 404 on determining that the first digital signal DATA1 has not changed over a period of time. The maintenance of the voltage VO at a constant voltage, reflected in a constant value of the first digital signal DATA1 (or the first digital signal DATA1 being maintained within a threshold range) may be used as a control input for the second ADC 404.

In some embodiments, the control module 406 may be configured to monitor a rate of change of the first digital signal DATA1 output from the first ADC 402. For example, if the rate of change of the first digital signal DATA1 exceeds a threshold change rate, the control module 406 may be configured to adjust or initiate operation of the second ADC 404 and/or output an interrupt signal IRQ. This may be particularly applicable where blood glucose is being measured in the electrochemical cell 401. In such scenarios, a high rate of change of the sampled voltage VO may be indicative of a blood glucose event, such as a hypoglycaemic event.

In addition to or instead of controlling sampling of the sample voltage VO by the second ADC 404, in response to activity (or inactivity) of the first digital signal DATA1 as discussed above, the control module 406 may be configured to send one or more interrupt signals IRQ to the transmitter 408 responsive to such activity (or inactivity). The transmitter 408 may be configured to transmit one or more signals to the host device 401, such as the second digital signal DATA2 and/or the interrupt signal(s) IRQ in response to receiving the interrupt signal(s) IRQ from the control module 406.

The control module 406 may be configured to control the second ADC 404 in one or more of the following exemplary ways.

In some embodiments, the control module 406 may be configured to trigger the second ADC 404 to sample the voltage VO. In such circumstances, the second ADC 404 may only sample the voltage VO at the sampling node NS in response to an enable signal EN received from the control module 406.

In some embodiments, the control module 406 may be configured to control a rate of sampling of the second ADC 404. For example, the control module 406 may be configured to increase or decrease the rate of sampling of the second ADC 404. For example, the rate of sampling by the second ADC 404 may be increased in response to a determination of a change or rate of change of the first digital signal DATA1 being above a threshold change or rate of change. It may be desirable to sample the voltage VO more often using the second (more accurate) ADC 404 during periods in which the voltage VO, as measured by the first ADC 402, is changing more quickly.

Additionally or alternatively, the control module 406 may be configured to decrease the rate of sampling of the second ADC 404 in response to a determination that a change or rate of change in the first digital signal DATA1 is below a predetermined threshold change or rate of change. For example, if the first digital signal DATA1 has stayed within a threshold range over a predetermined time period, the control module 406 may decrease the rate at which the second ADC 404 samples the voltage VO.

By adjusting the rate of sampling of the voltage VO by the second ADC 404, power consumption by the second ADC 404 may be minimized during periods in which the sample voltage VO is stable and increased during periods in which the sample voltage VO is less stable. The overall power consumption of the circuitry 400 may therefore be minimized whilst providing increased granularity in measurement during times of most importance (i.e. when the voltage VO is changing and/or changing quickly).

As mentioned above, in some embodiments, the transmitter 408 may be configured to transmit one or more signals to the host device 410 responsive to a change in the first digital signal DATA1, the interrupt signal(s) IRQ and/or the second digital signal DATA2. Transmission by the transmitter 408 may be controlled directly in response to receipt of the first and/or second digital signals DATA1, DATA2 or in response to a command from the control module 406. Such a command may be comprised in the interrupt signal(s) IRQ received from the control module.

In some embodiments, the transmitter 408 may be configured to periodically transmit the first digital signal DATA1 and/or the second digital signal DATA2 to the host device 410. As with the sampling of voltage VO by the second digital signal DATA2, the interval between transmissions may be increased and/or decreased in response to activity in the first digital signal DATA1. For example, where the second digital signal DATA2 is being updated more regularly due to the sampling rate of the second ADC 404 increasing, the transmitter 408 may transmit the second digital signal DATA2 from the second ADC 404 more regularly. Conversely, where the second digital signal DATA2 is being updated less regularly, the transmitter 408 may transmit the second digital signal DATA2 from the second ADC 404 less regularly. In doing so, power consumption can be minimised during times in which the voltage VO at the sample node NS is either not changing, changing slowly, or being maintained within a threshold range. During times where changes in the voltage VO are changing, changing more quickly, and/or moving outside of a threshold range, samples of the voltage VO may be sent by the transmitter 408 to the host device 410 more regularly for further processing.

In some embodiments, the control module 406 may be configured to transmit an interrupt signal IRQ to the transmitter 408 at the same time as causing the second ADC 404 to sample the sampling node NS.

The electrochemical cell 401 may be implemented using any known technology. For example, the electrochemical cell 401 may be incorporated into an analyte sensor. The analyte sensor may be an electrochemical aptamer-based sensor. In such sensors, DNA or RNA aptamers are fixed to the working (or interrogating) electrode. A redox reaction at the electrode surface is reported by a redox tag. Upon target binding, the aptamer changes structure by folding, bringing the redox reporter closer to the working electrode. This increase in proximity from the redox reporter to the working electrode enables faster electron transfer from the redox tag to the working electrode. The increase in speed of electron transfer contributes to a change in current that is detected by the electrochemical cell 401.

In other embodiments, the electrochemical cell 401 may be a glucose oxidase-based cell. In other embodiments, the analyte may be one of a ketone, oxygen or a lactate.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog TM or VHDL (Very high-speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general-purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

The invention claimed is:

1. Circuitry for processing an analyte signal obtained from an electrochemical cell, the circuitry comprising:
- a first analog-to-digital converter (ADC) configured to generate a first digital output based on the analyte signal;
- a second ADC configured to generate a second digital output based on the analyte signal;
- control circuitry configured to control generation of the second digital output by the second ADC based on the first digital output from the first ADC; and
- integration circuitry configured to:
  - integrate the first digital output to obtain an integrated first digital output; and
  - add the integrated digital output to the second digital output.

2. Circuitry of claim 1, wherein the second ADC has a higher resolution than the first ADC.

3. Circuitry of claim 1, wherein the first ADC consumes less power when generating the first digital output than the second ADC consumes when generating the second digital output.

4. Circuitry of claim 1, wherein the first ADC is asynchronous.

5. Circuitry of claim 1, wherein the first ADC is configured to sample the analyte signal at a first sampling rate, the second ADC is configured to sample the analyte signal at a second sampling rate slower than the first sampling rate.

6. Circuitry of claim 1, wherein the control circuitry is configured to control generation of the second digital output by the second ADC in response to a change in the first digital output from the first ADC.

7. Circuitry of claim 6, wherein the control circuitry is configured to control the generation of the second digital output by the second ADC in response to the change in the first digital output from the first ADC exceeding a threshold change or in response to the first digital output falling below a threshold limit.

8. Circuitry of claim 6, wherein the control circuitry is configured to control generation of the second digital output by the second ADC in response to a rate of change in the first digital output from the first ADC exceeding a threshold rate.

9. Circuitry of claim 6, wherein the control circuitry is configured to increase a sampling rate of the second ADC in response to an increase in the first digital output.

10. Circuitry of claim 1, wherein the control circuitry is configured to control the generation of the second digital output by the second ADC in response to a change in the first digital output from the first ADC being below a change threshold during a change interval.

11. Circuitry of claim 1, wherein controlling generation of the second digital output by the second ADC comprises:
- triggering the second ADC to sample the analyte signal to generate the second digital output; or
- powering up or activating the second ADC.

12. Circuitry of claim 1, further comprising:

a transmitter configured to transmit one or more of an interrupt signal, the first digital output and the second digital output to a host device.

13. Circuitry of claim 12, wherein the control circuitry is configured to control the transmitter to transmit the interrupt signal to the host device based on the first digital output from the first ADC or based on the second digital output from the second ADC.

14. Circuitry of claim 13, wherein the control circuitry is configured to control the transmitter to transmit the interrupt signal to the host device if the second digital output is within a threshold range of the first digital output.

15. Circuitry of claim 1, wherein the control circuitry is configured to combine the first digital output with the second digital output between updates of the second digital output by the second ADC.

16. Circuitry of claim 1, wherein an analyte of the analyte signal is one of glucose, ketone, oxygen or lactate.

17. Circuitry of claim 1, wherein the first ADC is an event driven ADC.

18. An analyte sensor comprising the circuitry of claim 1.

19. The analyte sensor of claim 18, wherein the analyte sensor is an electrochemical aptamer-based sensor or a glucose oxidase-based sensor.

20. A system comprising:

the analyte sensor of claim 18; and a host device in wireless communication with the analyte sensor.

21. A continuous glucose monitor comprising the analyte sensor of claim 18.

22. Circuitry for processing an analyte signal obtained from an electrochemical cell, the circuitry comprising:

a first analog-to-digital converter (ADC) configured to generate a first digital output based on the analyte signal;

a second ADC configured to periodically generate a second digital output based on the analyte signal;

integration circuitry configured to:

integrate the first digital output to obtain an integrated first digital output; and add the integrated digital output to the second digital output; and control circuitry configured to:

monitor the first digital output or the second digital output between periodic generation of the analyte signal by the second ADC; and in response to the first digital output or the second digital output meeting one or more criteria, output an interrupt signal.

23. Circuitry of claim 22, wherein the one or more criteria comprises one of:

a) the first digital output falling below a threshold level;

b) the first digital output exceeding a threshold level;

c) the first digital output moving outside of a threshold range;

d) the first digital output changing at a rate exceeding a threshold rate.

24. Circuitry of claim 22, wherein the first ADC is configured to periodically generate the first digital output at a first sampling rate, and the second ADC is configured to periodically generate the second digital output at a second sampling rate slower than the first sampling rate.

25. Circuitry of claim 22, wherein the first ADC is asynchronous.

26. Circuitry of claim 22, further comprising a transmitter, wherein the interrupt signal is output to the transmitter.

27. Circuitry of claim 22, wherein the control circuitry is configured to reset the integration circuitry on generation of the second digital output by the second ADC.

28. Circuitry of claim 22, wherein the control circuitry is configured to output the interrupt signal in response to the second digital output.

* * * * *